(12) United States Patent
Deshpande et al.

(10) Patent No.: US 6,552,213 B1
(45) Date of Patent: Apr. 22, 2003

(54) STEREOSELECTIVE ROUTE TO PRODUCE TRIS-O-SUBSTITUTED-(E)-1-(3,5-DIHYDROXYPHENYL)-2-(4-HYDROXYPHENYL)ETHENE, AN INTERMEDIATE IN THE SYNTHESIS OF TRANS-RESVERATROL

(75) Inventors: Pandurang Balwant Deshpande, Chennai (IN); Udayampalayam Palanisamy Senthilkumar, Chennai (IN); Gnanaprakasam Andrew, Chennai (IN)

(73) Assignee: Orchid Chemicals & Pharmaceuticals Limited, India (IN)

( * ) Notice: Subject to any disclaimer, the term of this patent is extended or adjusted under 35 U.S.C. 154(b) by 0 days.

(21) Appl. No.: 10/153,681

(22) Filed: May 24, 2002

(51) Int. Cl.$^7$ .................................................. C07F 7/08
(52) U.S. Cl. ..................... 556/440; 556/443; 556/444; 556/446; 556/486; 560/254; 560/255; 568/607; 568/630; 568/631; 568/636; 568/659; 568/660

(58) Field of Search ................................. 556/440, 443, 556/444, 446, 486; 560/254, 255; 568/607, 630, 631, 636, 659, 660

(56) References Cited

U.S. PATENT DOCUMENTS 5,998,563 A * 12/1999 Pirwitz et al. .............. 556/440

* cited by examiner

Primary Examiner—Paul F. Shaver
(74) Attorney, Agent, or Firm—Oliff & Berridge, PLC

(57) ABSTRACT

The present invention relates to a new stereoselective method for the preparation of tris-O-substituted-(E)-1-(3,5-dihydroxyphenyl)-2-(4-hydroxyphenyl)ethene derivative of the formula (I) which is a key intermediate in the synthesis of trans-resveratrol (I, $R^2=R^2=R^3=H$). The invention also provides a method for the exclusive synthesis of trans-isomer of compounds of formula (I) without any contamination of cis-isomer.

20 Claims, No Drawings

STEREOSELECTIVE ROUTE TO PRODUCE TRIS-O-SUBSTITUTED-(E)-1-(3,5-DIHYDROXYPHENYL)-2-(4-HYDROXYPHENYL)ETHENE, AN INTERMEDIATE IN THE SYNTHESIS OF TRANS-RESVERATROL

FIELD OF THE INVENTION

The present invention relates to a new stereoselective method for the preparation of tris-O-substituted-(E)-1-(3,5-dihydroxyphenyl)-2-(4-hydroxyphenyl)ethene derivative of the general formula (I) which is a key intermediate in the synthesis of trans-resveratrol (I, $R^2=R^2=R^3=H$). The invention also provides a method for the exclusive synthesis of trans-isomer of compounds of general formula (I) without any contamination of cis-isomer.

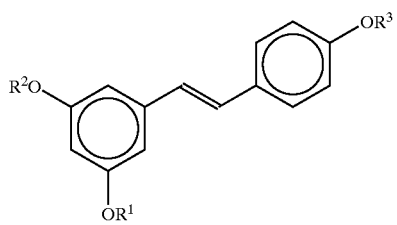

(I)

BACKGROUND OF THE INVENTION

Polyhydroxylated trans-stilbenes, the natural products, have been found to exhibit interesting biological activities. Trans-resveratrol has been found to raise the level of high-density lipoproteins (HDL) and lower the level of low-density lipoproteins (LDL) in human beings thereby reducing the risk of clogging arteries and consequent myocardial infarctions (Toppo, F. U.S. Pat. No. 6,048,903). Many 5-alkenyl resorcinols show antileukemic activity (Alonso, E; Ramon, D. J; Yus, M. *J. Org. Chem.* 1997, 62, 417–421; Thakkar, K; Geahlen, R. L.; Cushman, M. *J. Med. Chem.* 1993, 36(20), 2950–2955) and anti-tumor properties (He, K.; Zheng, Q. Y.; Zheng, B. L.; Kim, C. H. WO 2000/037021). Plant material containing trans-resveratrol has been used as a herbal medicine for the treatment of hyperlupemia and liver diseases in China and Japan for many centuries (Kimura, K. M. et al. *Shoyqakugaku Zasshi* 1987, 83, 35–58).

Further investigations led to identification of many important biological functions including inhibition of lypooxygenase activity (Kimma, Y. et al. *Biochem. Biophys. Acta.* 1985, 834, 275), inhibition of anaphylactoid (Ragazy et al. *Pharmacol. Ref. Commun.* 1988, 79, 20) and protection of lipoproteins against oxidative and free radical damage (Frankel E. N. et al. *Lancet* 1979, 1, 1017).

It has been reported that piceatannol, a known antileukemic principle in the seeds of *Euphorbia lagascae*, inhibits the PTK (protein-tyrosine kinase) activities of P40 as well as P56[lck] by binding to the substrate binding sites (Geahlen, R. L.; McLaughlin, J. L. *Biochem. Biophys. Res. Commun.* 1989, 165, 241–245). Thakkar et al. studied a series of hydroxylated trans-stilbenes and reported enhanced activity for inhibition of the lymphoid cell lineage-specific protein-tyrosine kinase P56[lck] which plays an important role in lymphocyte proliferation and immune function.

In view of the vital biological activities of the polyhydroxylated trans-stilbenes, there have been a few methods reported for the synthesis of these compounds. For example, trans-resveratrol is synthesized by the Wittig reaction of 3,5-dimethoxybenzyltriphenyl phosphonium salt with p-anisaldehyde in the presence of n-butyl lithium. The mixture of cis-and trans olefins so obtained is demethylated with large amount of boron tribromide to get very low yield of the product (Toppo, F. U.S. Pat. No. 6,048,903). This method suffers from the low yield, low quality and use of expensive and hazardous reagents, which prevents from employing this method on commercial scale. Similar low yields are reported employing condensation of phosphonate esters with aromatic aldehydes followed by demethylation using pyridine hydrochloride (WO 2000/021368). In case of piceatannol, tetramethoxystilbene precursor is synthesized by the Witting reaction and the methyl groups are then removed by demethylation reaction with pyridine hydrochloride (Drewes, S. E; Fletcher, I. P. *J. Chem. Soc. Perkin Trans. I*, 1974, 961–962) or with boron tribromide (Bajaj, R; Gill, M. T.; McLaughlin, J. L. *Rev. Latinoamer Quim.* 1987, 18, 79–80).

Use of trimethylsilyl protecting groups followed by witting reaction to get the hydroxy-trans-stilbene products has also been reported (Reimann, E. *Tetrahedron Lett.* 1970, 4051–4053). Yet another route comprising the reaction of 3,5-dihydroxyphenylacetate and 3,4-dihydroxybenzaldehyde in acetic anhydride, decarboxylation of the ensuing 3,3', 4,5'-tetraacetoxystilbene-α-carboxylic acid with copper and quinoline at high temperature, and hydrolysis of the resulting piceatannol tetraacetate with sodium hydroxide is also reported. (Cunningham, J; Haslam, E; Haworth, R. D. *J. Chem. Soc.* 1963, 2875–2883). All these processes for the preparation of trans-resveratrol are reported to proceed in moderate to low yields.

In those cases where Wittig reactions are employed, the undesired cis-isomers are also formed along with the desired trans-isomers to the extent of 52% (trans 48%) when potassium t-butoxide is employed (Ali, M. A.; Kondo, K; Tsuda, Y. *Chem. Pharm. Bull.* 1992, 40(5), 1130–1136). Similarly, cis isomers are formed to the extent of 45% (trans:23%) when sodium hydride is used. (Cushman, M; Nagarathnam, D; Gopal D. et al. *J. Med. Chem.* 1992, 35(12), 2293–2306; Chen, Yi-Ping; Lei, Tong-Kang. *Zhongquo Yiyao Gongye Zazhi* 2000, 31(7), 334–336.

In another process, 3,5-dimethoxybenzyl trimethylsilyl ether is treated with lithium metal in the presence of p-anisaldehyde to yield, after dehydration, 3,4',5-trimethoxystilbene, a penultimate intermediate which requires excess boron tribromide (Alonso, E; Ramon, D. J.; Yus, M. *J. Org. Chem.* 1997, 62(2), 417–421). Similar use of excess boron tribromide has been indicated in WO 01/60774.

A wide variety of demethylating reagents such as boron tribromide, boron tribromide-dimethyl sulfide complex, boron trichloride-dimethyl sulfide complex, pyridine hydrochloride with a catalytic amount of quinoline at elevated temperatures, methyl magnesium iodide etc., are employed. In all these cases, demethylation is always incomplete and the yields and quality are disappointing. To purify the product obtained after dealkylation, costly chromatographic techniques were employed (Thakkar, K; Geahlen, R. L; Cushman, M. *J. Med. Chem.* 1993, 36(20), 2950–2955).

In the synthesis, which involves the Wittig reaction, the mixture of cis- and trans-isomers are separated by column chromatography or irradiated a solution of the mixture to convert cis into trans isomers.

These processes are commercially and technically difficult to be implemented. In addition, main problems in the synthesis of these polyhydroxylated-1,2-diphenylethenes are caused by the instability of this polyphenolic stilbene due to its oxidation, resulting in the formation of unstable radicals and quinones. The final isolation of the product has to therefore be carried out from dark coloured mixture containing multiple components.

OBJECTIVES OF THE INVENTION

The objective of the present invention is to develop a commercial method for preparing polyhydroxy-1,2-diphenylethenes, especially (E)-1-(3,5-dihydroxyphenyl)-2-(4-hydroxyphenyl)ethene, with exclusive trans stereo chemistry.

Another objective of the present invention is to overcome the technical difficulties associated with the reported methods and develop a commercial process to manufacture exclusively the trans-isomer.

Yet another objective of the present invention is to provide a simple and effective process without using photochemical reaction in the manufacturing process.

Still another objective is to avoid the use of expensive and hazardous chemicals viz. boron tribromide, lithium, Lithium aluminum hydride, sodium hydride, triethyl phosphite, phosphorus tribromide, etc. in the present process.

SUMMARY OF THE INVENTION

The present invention relates to a process for the stereoselective synthesis of tris-O-substituted-(E)-1-(3,5-dihydroxyphenyl)-2-(4-hydroxy phenyl)ethene derivatives of general formula (I), wherein those disadvantages, which have plagued this art, are obviated.

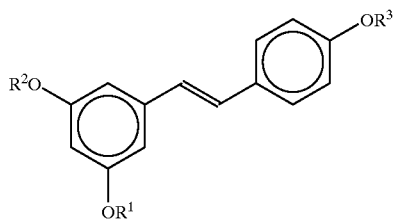

(I)

wherein $R_1$, $R_2$, and $R_3$ are independantly represented as alkoxyalkyl, allyl, vinyl, silyl, formyl, acyl, arylalkyl or substiuted arylalkyl groups or a combination thereof.

Moreover, the foregoing technique has been found to be markedly attractive, both from commercial point of view, as well as from a stereo selectivity standpoint, and affords an almost exclusive formation of the trans-isomer and is also free from the limitations discussed above.

The subject compounds of general formula (I) are eminently well suited as intermediates to manufacture (E)-1-(3,5-dihydroxyphenyl)-2-(4-hydroxyphenyl)ethene (I; $R^1,R^2,R^3$=H) for carrying out the process of the invention. Moreover, the preparation of this can be accomplished quite easily and inexpensively.

Accordingly, the compounds of general formula (I) of the present invention are useful as intermediates for the production of (E)-1-(3,5-dihydroxyphenyl)-2-(4-hydroxyphenyl) ethene (I; $R^1,R^2,R^3$=H) which has broad spectrum biological activity.

DETAILED DESCRIPTION OF THE INVENTION

The present invention relates to a stereoselective process for the preparation of substituted diaryl ethenes and more specifically tris-O-substituted-(E)-1-(3,5-dihydroxyphenyl)-2-(4-hydroxy phenyl)ethene derivative of general formula (I),

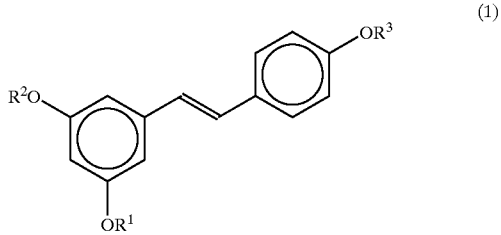

(1)

wherein $R^1$, $R^2$ and $R^3$ are independently represented as alkoxyalkyl, allyl, vinyl, silyl, formyl, acyl, arylalkyl or substituted arylalkyl groups or a combination thereof, the said process comprising steps of:

a) treating compound of formula (III) with halogenating agent in an organic solvent under nitrogen atmosphere for a period of 60–180 minutes,

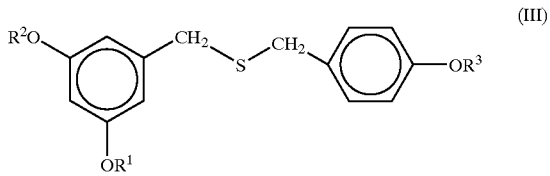

(III)

wherein $R_1$, $R_2$ and $R_3$ are as defined above, b) removing the precipitated byproduct of step (a) by filtration to get a solution.

c) evaporating the solution of step (b) to remove the solvent, to obtain a residue, d) dissolving the residue of step (c) residue in an dry organic solvent, e) treating the solution of step (d) with an oxidizing agent, at a temperature between −30° C. to +60° C. for a time period of 15–300 minutes, f) quenching the reaction mixture of step (e) with ice, thereby forming an organic layer and an aqueous layer, g) separating the organic layer of step (f), h) washing the organic layer of step (g) with an aqueous alkali bicarbonate solution followed by water, i) charcoalizing the organic layer of step (h), filtering and removing the organic solvent under vacuum to obtain compound of general formula (IV)

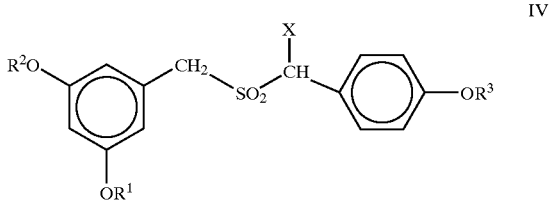

IV wherein X is halogen and $R_1$ to $R_3$ are defined as above j) treating the compound of formula (IV) of step (i) with a phase transfer catalyst and a base in an organic solvent at a temperature in the range of −60° to +110° C., for a period of 15–480 minutes, k) adding water to the reaction mixture of step (j), l) separating the organic layer from the reaction mixture of step (k), charcoalizing, filtering, and evaporating the organic layer to obtain a residue, and m) treating the residue of step (l) with alcoholic solvent at a temperature range of 25°–32° C. for 1–3 hours to obtain exclusively a stereoselective trans form tris-O-substituted (E)-1-(3,5-dihydroxyphenyl)-2-(4-hydroxyphenyl)ethene derivative represented by general formula (I).

In another embodiment, the compound of general formula (I), is alternatively prepared by a process comprising steps of oxidising compound of formula (III) using an oxidising agent in a medium containing aqueous organic acid at a temperature in the range of −30° to +60° C. for a period of 15–300 minutes, followed by quenching the reaction mixture into ice and performing steps (g) to (l) of claim 1 to obtain compound of formula (II), which is further treated with a phase transfer catalyst, halogenating reagent and in an organic solvent at a temperature in the range of −60° to +110° C. for a period of 15 to 480 minutes, followed by adopting steps (k) to (m) of claim 1 to obtain exclusively stereoselective form of tris-O-substituted (E)-1-(3,5-dihydroxy phenyl)-2-(4-hydroxyphenyl)ethene derivatives represented by general formula (I).

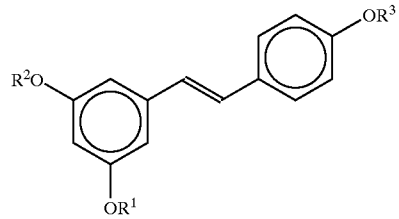

The process adopted for the preparation of compound of formula (I) is depicted in a flow chart (Scheme I) as shown below:

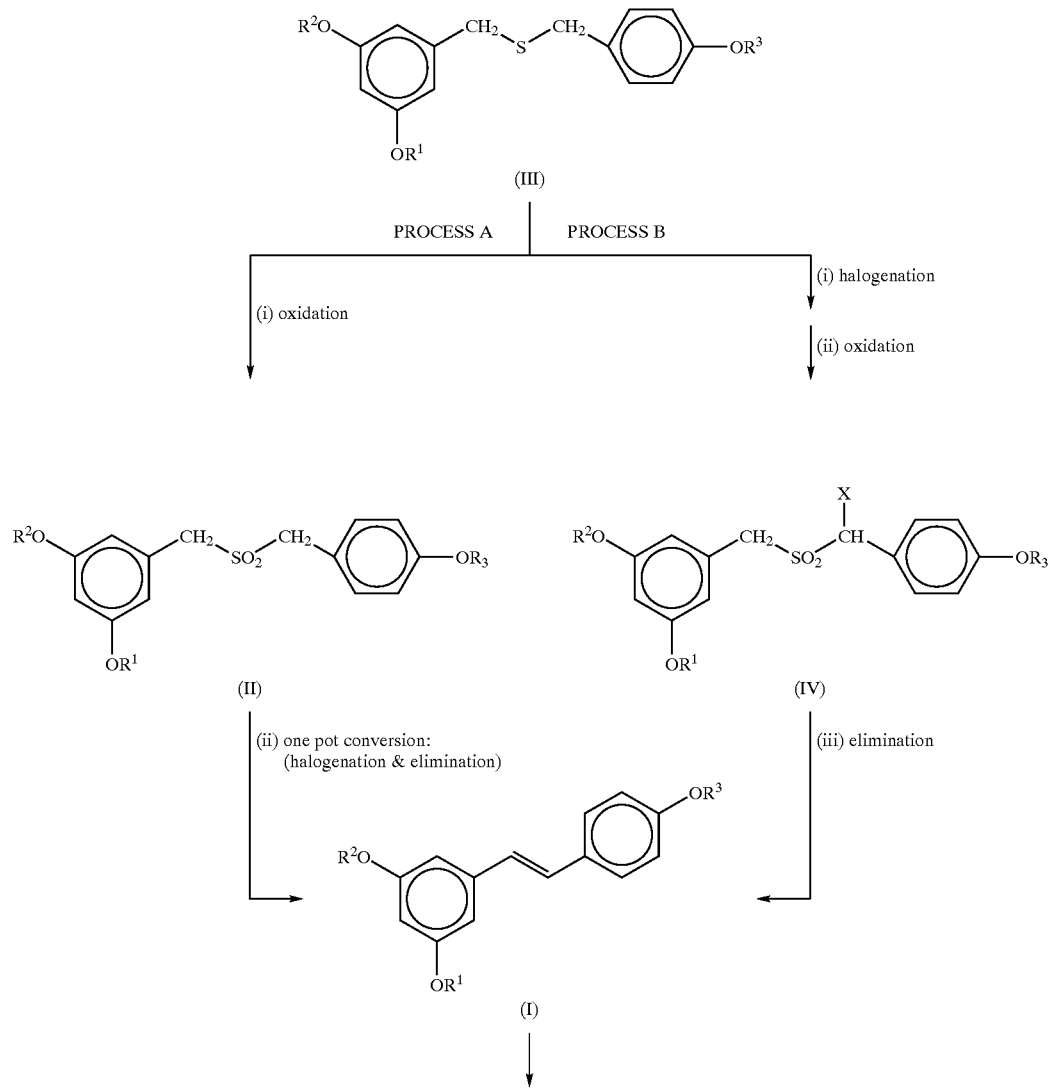

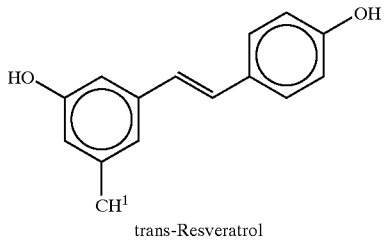

trans-Resveratrol

The groups, $R^1$, $R^2$ and $R^3$, which represent a protecting group for the hydroxyl groups in the compounds of the formulae (I)–(IV) are arylalkyl, allyl or silyl groups which can be removed selectively without disturbing the double bond and more particularly, the stereochemistry with respect to the double bond. Since the protecting group ultimately is to be cleaved, it is desirable that the protecting group be easily cleaved in an optional step after the preparation of compound (I). It is further required that the protecting group be stable during the olefination reaction during halogenation and alkali-treatment. In this respect arylalkyl, allyl, vinyl and silyl groups are useful protecting groups. In addition alkoxymethyl, acetyl and formyl groups are the alternate choices.

In another embodiment, the present invention provides the use of 3,4,5-tri-O-substituted dibenzyl sulphide as a starting material for the synthesis of tris-O-substituted-(E)-1-(3,5-dihydroxyphenyl)-2-(4'-hydroxyphenyl)ethene derivative and trans-reseveratrol.

In one another embodiment, the present invention provides method for performing the oxidation reaction at a temperature in the range of −30° C. to +60° C. and preferably 15° to 25° C.

In an another embodiment, the present invention provides the use of an oxidizing agent for carrying out oxidation selected from the group consisting of hydrogen peroxide, potassium permanganate, peracetic acid, trifluoroperacetic acid and m-chloroperbenzoic acid.

In one another embodiment, the present invention provides the use of an halgenating reagent for carrying out halogenation reaction selected from the group consisting of chlorine, carbon tetrachloride, sulfuryl chloride, phosphorous (V) chloride, N-chlorosuccinimide and N-bromosuccinimide.

In a further embodiment, the present invention provides temperature for performing the halogenation reaction in a range of −60 to +110° C. and preferably between 20°–45° C.

In yet another embodiment, the present invention provides the use of organic solvent in carrying out the reaction selected from the group consisting of chloroform, dichloromethane, benzene, toluene, tetrahydrofuran and dioxane.

In still another embodiment of the present invention, base used is selected from the group consisting of alkali metal hydroxide, alkaline earth metal hydroxide, and secondary/tertiary amine organic bases.

In still yet another embodiment, the present invention provides the use of phase transfer catalyst to promote the reaction, preferably lipophilic phase transfer catalyst selected from the group consisting of quaternary ammonium salts and crown ethers.

In still another embodiment, the present invention provides the use of preferably equimolar ratio of halogenating agent and the substrate (Process B).

In still another embodiment, the present invention provides the use of excess halogenating agent to enhance the rate of reaction and quality of the product (Process A).

In still one more embodiment, the present invention provides the relative mole equivalents of compound (II) and base as in the range of 1:1 to 1:4.

In still another embodiment, the present invention provides the reaction time for completion in the range of 15 minutes to 480 minutes.

In one more embodiment, the present invention provides the preparation of an intermediate α-halosulphone derivative of formula (IV) in the Process B.

The present invention is illustrated with following examples, which should not be construed as limiting to the scope of the invention.

EXAMPLE 1

Preparation of 3,4',5-Tribenzyloxydibenzylsulfone (II)

To a round-bottomed flask equipped with a thermometer and an agitator is added acetic acid (400 ml) and cooled to 15–25° C. To the stirred solution, 3,4',5-tribenzyloxydibenzylsulfide (50 gm) is added slowly. To this solution, water (40 ml) is added at 15–25° C. followed by potassium permanganate slowly over a period of 2 hours until the pink color persists. The reaction is followed by TLC. After the reaction is over, the mixture is quenched into ice (500 gm) and decolorized with 25% $H_2O_2$ solution. The organic layer is separated and washed with DM water, saturated bicarbonate solution and DM water at 10–15° C. The MDC layer is charcoalized, evaporated to a paste which is stirred with isopropyl ether (200 ml) to get 3,4',5-tribenzyloxydibenzylsulfone.

EXAMPLE 2

Preparation of (E)-1-[4-(Benzyloxy)phenyl]-2-[3,5-bis(benzyloxy)phenyl]ethene (I)

To a round-bottomed flask equipped with a thermometer and an agitator are added sodium hydroxide solution (10%, 850ml), aliquat 336 (15 gm) and dichloromethane (500 ml). To the clear biphasic solution thus obtained, is added 3,4',5-tribenzyloxydibenzylsulfone (100 gm) in dichloromethane (850 ml) in 10–20 minutes with stirring. Then carbon tetrachloride (450 ml) is added in 20 minutes at 25°–30° C. Temperature is raised to 40–45° C. and further maintained for 45 minutes. The reaction is monitored by TLC. After the reaction is over, organic layer is separated and washed with DM water (500 ml) three times followed by brine (500 ml).

To the dichloromethane layer, charcoal (5 gm) is added, stirred at 25°–28° C. for 15–20 minutes, filtered and evaporated under vacuum at <30° C. to yield a residue. To the crude residue, methanol (300 ml) is added, stirred for 1 hour at 25–32° C. and filtered. The product is dried under vacuum at 25–32° C. for 6 hours to get (E)-1-[4-(benzyloxy)

phenyl)]-2-[3,5-bis(benzyloxy)phenyl]ethene in an exclusive trans form. Mp. 156–158° C.; $^1$H NMR (CDCl$_3$, 400 MHz): δ 5.09 (s, 4H), 5.11 (s, 2H), 6.56 (t, J=2.1 Hz, 1H), 6.77 (d, J=2.1 Hz, 2H), 6.91 (d, J=16.2 Hz, 1H), 6.99 (d, J=8.7 Hz, 2H), 7.04 (d, J=16.2 Hz, 1H), 7.34–7.48 (m, 17H); Mass m/e: 498.2. HPLC confirms that the cis-isomer content is <0.01% [for HPLC analysis, reference sample of cis-isomer is synthesized by a different procedure and the stereochemistry and structure confirmed by $^1$H NMR].

EXAMPLE 3

Preparation of (E)-1-(3,5-Dihydroxyphenyl)-2-(4-hydroxyphenyl)ethene (trans-Resveratrol)

In a 3 lit. round-bottomed flask equipped with a thermometer are added aluminum chloride (390.35 gm) and N,N-dimethylaniline (413.10 gm) maintaining the temperature at 40–50° C.(exothermic). To this solution, (E)-1-[4-(benzyloxy)phenyl]-2-[3,5-bis(benzyloxy)phenyl]ethene (243 gm) in dichloromethane (800 ml) is added and stirred for further 0.75 hour. After the reaction is over, the reaction mixture is quenched into dil. hydrochloric acid at 0–5° C. and extracted with ethyl acetate. The organic layer is charcoalized and concentrated to get pure (E)-1-(3,5-dihydroxyphenyl)-2-(4-hydroxyphenyl)ethene (trans-Resveratrol) in the exclusive trans form. Mp 257–259° C. $^1$H NMR (DMSO-d6, 400 MHz) δ 6.11 (t, J=1.8 Hz, 1H), 6.38(d, J=1.8 Hz, 2H), 6.75 (d, J=8.5 Hz, 2H), 6.82(d, J=16.3 Hz, 1H), 6.92(d, J=16.3, 1H), 7.39(d, J=8.4 Hz, 2H); Mass M/e:228.2

EXAMPLE 4

Preparation of α-Chloro-3,4',5-tribenzyloxydibenzylsulfone (IV).

Into a round-bottomed flask equipped with a thermometer, and guard tube under nitrogen atmosphere are added 3,4',5-tribenzyloxydibenzylsulfide (53.2 gm) and carbon tetrachloride (250 ml) at 28–30° C. N-Chlorosuccinimide (13.35 gm) is added and stirred well until the reaction is over. The reaction is monitored by TLC. After the reaction is over, the reaction mixture is filtered to remove succinimide and distilled under vacuum until a residue is obtained. The residue is dissolved in dry dichloromethane and cooled to −10° C. A dry solution of peracetic acid in dichloromethane is added slowly over a period of 2 hours at −10 to −5° C. The temperature is raised to 25° C., maintained at this temperature for 10–15 minutes and further raised to 40° C. The reaction is followed by tic. After the reaction is over, the reaction mixture is quenched into ice (750 gm). The organic layer is separated and washed with DM water, saturated sodium bicarbonate solution and DM water at 10–15° C. The MDC layer is charcoalized and concentrated under vacuum to get α-chloro-3,4',5-tribenzyloxydibenzylsulfone which is used in next step as such.

EXAMPLE 5

Preparation of (E)-1-[4-(Benzyloxy)phenyl]-2-[3,5-bis(benzyloxy)phenyl]ethene (I)

To a round-bottomed flask equipped with a thermometer and an agitator are added sodium hydroxide solution (10%, 850 ml), aliquat 336 (15 gm) and dichloromethane (500 ml). To the clear biphasic solution, thus obtained is added to α-chloro-3,4',5-tribenzyloxydibenzylsulfone (100 gm) in dichloromethane (850 ml) in 10–20 minutes with stirring. Temperature is raised to 40–45° C. and further maintained for 45 minutes. The reaction is monitored by TLC. After the reaction is over, organic layer is separated and washed with DM water (500 ml) three times followed by brine (500 ml).

To the dichloromethane layer, charcoal (5 gm) is added, stirred at 25°–28° C. for 15–20 minutes, filtered and evaporated under vacuum at <30° C. to yield a residue. To the crude residue, methanol (300 ml) is added, stirred for 1 hour at 25–32° C. and filtered. The product is dried under vacuum at 25–32° C. for 6 hours to get (E)1-[4-(benzyloxy)phenyl)]-2-[3,5-bis(benzyloxy) phenyl]ethene in an exclusive trans form. Mp.156–158° C.; $^1$H NMR (CDCl$_3$, 400 MHz): δ 5.09 (s, 4H), 5.11 (s, 2H), 6.56 (t, J=2.1 Hz, 1H), 6.77 (d, J=2.1 Hz, 2H), 6.91 (d, J=16.2 Hz, 1H), 6.99 (d, J=8.7 Hz, 2H), 7.04 (d, J=16.2 Hz, 1H), 7.34–7.48 (m, 17H); Mass m/e: 498.2. HPLC confirms that the cis-isomer content is <0.01% [for HPLC analysis, reference sample of cis-isomer is synthesized by a different procedure and the stereochemistry and structure confirmed by $^1$H NMR].

MAIN ADVANTAGES OF THE PRESENT INVENTION

1. The process of the present invention does not involve the use of expensive and hazardous reagents.
2. The process of the present invention provides exclusively trans isomer of tris-O-substituted-(E)-1-(3,5-dihydroxy phenyl)-2-(4-hydroxy phenyl)ethene.
3. The present invention also provides easy and cheap process for the purification of the required intermediate trans isomer.

What is claimed is:

1. A stereoselective process for the preparation of substituted diarylethenes represented by general formula (I)

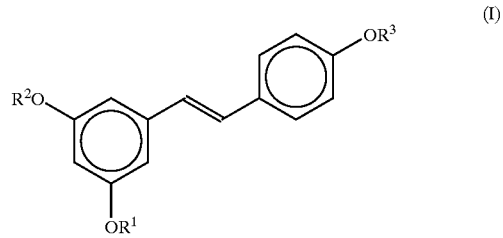

a) wherein R$^1$, R$^2$ and R$^3$ are independently represented as alkoxyalkyl, allyl, vinyl, silyl, formyl, acyl, arylalkyl or substituted arylalkyl groups, or a combination thereof, the said process comprising the steps of:
b) treating a compound of formula (III) with a halogenating agent in an organic solvent under nitrogen atmosphere for a period of 60–180 minutes,

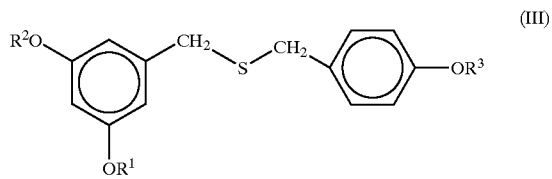

wherein R$_1$, R$_2$ and R$_3$ are as defined above,
c) removing the precipitated by product of step (a) by filtration to get a solution,
d) evaporating the solution of step (b) to remove the solvent, to obtain a residue,
e) dissolving the residue of step (c) residue in an dry organic solvent, f) treating the solution of step (d) solution with an oxidizing agent, maintaining the temperature between −30° C. to +60° C. for a time period of 15–300 minutes, g) quenching the reaction mixture of step (e) with ice, thereby forming an organic layer and an aqueous layer, h) separating the organic layer of step (f), i) washing the organic layer of step (g) with an aqueous alkali bicarbonate solution followed by water, j) charcoalizing the organic layer of step (h), filtering and removing the organic solvent under vacuum to obtain compound of general formula (IV)

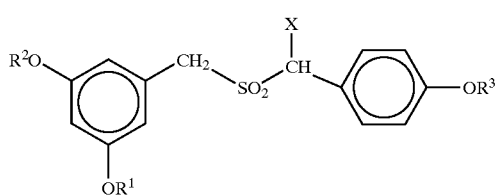

IV wherein X is halogen and $R_1$ to $R_3$ as defined above j) treating the compound of formula (IV) of step (i) with a phase transfer catalyst and a base in an organic solvent at a temperature range of −60° to +110°, for a period of 15–480 minutes, k) adding water to the reaction mixture of step (j), l) separating the organic layer from the reaction mixture of step (k), charcoalizing, filtering, and evaporating the organic layer to obtain a residue, and m) treating the residue of step (l) with alcoholic solvent at a temperature range of 25°–32° C. for 1–3 hours to obtain exclusively a stereoselective trans form tris-O-substituted (E)-1-(3,5-dihydroxyphenyl)-2-(4-hydroxyphenyl)ethene represented by general formula (I).

2. A process for the preparation of compound of general formula (I), said process comprising oxidising a compound of formula (III) using an oxidising agent in a medium containing aqueous organic acid at a temperature range of −30° to +60° C. for a period of 15–300 minutes, followed by quenching the reaction mixture and performing steps (g) to (l) of claim 1 to obtain a compound of formula (II) which is further treated with a phase transfer catalyst, halogenating reagent in an organic solvent at a temperature range of −60° to +110° for a period of 15 to 480 minutes, followed by adopting steps (k) to (m) of claim 1 to obtain exclusive stereoselective form of tris-O-substituted (E)-1-(3,5-dihydroxy phenyl)-2-(4-hydroxyphenyl) ethene represented by general formula (I).

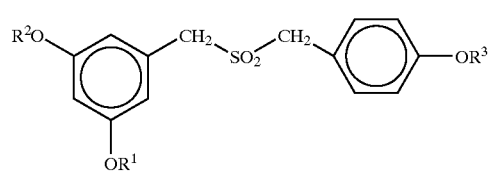

(II)

wherein $R_1$, $R_2$, and $R_3$ are as defined above.

3. A process as claimed in claim 1, wherein in step (a), the halogenating agent used is selected from a group consisting of chlorine, carbontetrachloride, sulfuryl chloride, phosphorous (V) chloride or N-bromosuccinimide and preferably carbontetrachloride.

4. A process as claimed in claim 1, wherein in step (a), the organic solvent used is selected from a group consisting of chloroform, dichloromethane, benzene, toluene, tetrahydrofuran or dioxane and preferably dichloromethane.

5. A process as claimed in claim 1, wherein in step (a), the halogenation reaction is performed preferably at a temperature range of 25°–45° C.

6. A process as claimed in claim 1, wherein in step (e), the oxidising agent used is selected from a group consisting of hydrogenperoxide, potassium permanganate, peracetic acid and m-chloro perbenzoic acid.

7. A process as claimed in claim 1, wherein in step (e), the oxidation reaction is performed preferably at a temperature range of 15° C.–25° C.

8. A process as claimed in claim 1, wherein in step (h), the alkali carbonate is selected from a group consisting of sodium bicarbonate, potassium bicarbonate, sodium carbonate, potassium carbonate and preferably sodium bicarbonate.

9. A process as claimed in claim 1 wherein in step (j), the phase transfer catalyst used is selected from a group consisting of crown ethers, quarternary ammonium salt and preferably aliquat 336 in biphasic or homogeneous medium.

10. A process as claimed in claim 1 wherein in step (j), the base used is selected from a group consisting of alkali metal hydroxide alkaline earth metal hydroxide secondary or tertiary amine organic bases.

11. A process as claimed in claim 1, wherein in step (m), the alcoholic solvent is selected from a group of methanol, ethanol, propanol, and preferably methanol.

12. A process as claimed in claim 2 wherein the oxidising agent used is selected from group consisting of hydrogenperoxide, potassium permanganate, peracetic acid or m-chloro perbenzoic acid and preferably peracetic acid.

13. A process as claimed in claim 2, wherein the aqueous organic acid used is aqueous acetic acid.

14. A process as claimed in claim 2, wherein the halogenating agent used is selected from a group consisting of chlorine, carbontetrachloride, sulfuryl chloride, phosphorous (V) chloride or N-bromosuccinimide and preferably carbontetrachloride.

15. A process as claimed in claim 2, wherein the phase transfer catalyst used is selected from a group consisting of crown ethers, quarternary ammonium and preferably aliquat 336 in biphasic or homogeneous medium.

16. A process as claimed in claim 2, wherein the base used is selected from a group consisting of alkali metal hydroxide alkaline earth metal hydroxide secondary or tertiary amine organic bases.

17. A process as claimed in claim 2, wherein the purification of resveratrol intermediate product is performed using alcoholic solvent selected from a group consisting of methanol, ethanol, propanol, and preferably methanol.

18. A process as claimed in claim 1, wherein in step (a) the ratio of the compounds of formula (II) and the halogenating reagent used is in the ratio of 1:2.5.

19. A process as claimed in claim 1, wherein in step (j) the ratio of compound of formula (ii) and alkali is in the range of 1:1 to 1:4.

20. A process as claimed in claim 2 wherein the use of excess halogenating agent promotes the rate of reaction and improves the quality of product.

* * * * *